United States Patent [19]

Rasberger et al.

[11] 4,221,701

[45] Sep. 9, 1980

[54] STABILIZED SYNTHETIC POLYMERS

[75] Inventors: Michael Rasberger, Allschwil; Jean Rody, Basel, both of Switzerland

[73] Assignee: Ciba-Geigy Corporation, Ardsley, N.Y.

[21] Appl. No.: 915,346

[22] Filed: Jun. 13, 1978

Related U.S. Application Data

[60] Continuation of Ser. No. 744,352, Nov. 23, 1976, abandoned, which is a division of Ser. No. 525,810, Nov. 21, 1974, Pat. No. 3,993,655.

[30] Foreign Application Priority Data

Dec. 10, 1973 [CH] Switzerland ............... 017271/73

[51] Int. Cl.$^2$ ................................................ C08K 5/34
[52] U.S. Cl. ............................................. 260/45.8 N
[58] Field of Search ................................. 260/45.8 N

[56] References Cited

U.S. PATENT DOCUMENTS

| | | | |
|---|---|---|---|
| 3,640,928 | 2/1972 | Murayama et al. | 260/45.8 N |
| 3,721,704 | 3/1973 | Dexter | 260/45.85 |
| 3,992,390 | 11/1976 | Holt et al. | 260/45.8 N |

*Primary Examiner*—V. P. Hoke
*Attorney, Agent, or Firm*—Harry Falber

[57] ABSTRACT

Esters of 2,2,6,6-tetramethylpiperidinols with mono- or bis-hydroxybenzylmalonic acids are powerful stabilizers for organic polymers, especially for polyolefins. They protect the polymers against thermal-oxidative degradation as well as against light-induced aging. Similar activity show the corresponding amides of hydroxybenzylmalonic acids. The esters and the amides can be prepared by analogous processes.

11 Claims, No Drawings

STABILIZED SYNTHETIC POLYMERS

This is a continuation of application Ser. No. 744,352 filed on Nov. 23, 1976 now abandoned, which latter application is a divisional of application Ser. No. 525,810, filed on Nov. 21, 1974, now U.S. Pat. No. 3,993,655.

The invention relates to new derivatives of hydroxybenzylmalonic acids, to their preparation, and to their use as stabilisers for synthetic polymers, as well as to the material stabilised with the aid of the said derivatives.

The compounds concerned are those of formula (I)

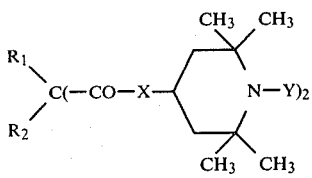

wherein

X can be oxygen or —NH—,

Y represents hydrogen, the radical —O., an alkyl group having 1 to 12 carbon atoms, an alkenyl group having 3 or 4 carbon atoms, a propargyl group, a benzyl group, or a group of the formula

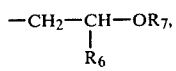

wherein $R_6$ represents hydrogen, methyl or phenyl, and $R_7$ represents hydrogen, or an acyl group having up to 18 carbon atoms, $R_1$ represents a hydroxybenzyl group of formula (II)

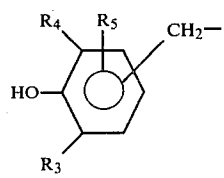

wherein $R_3$ and $R_4$ each independently represent an alkyl group having 1 to 8 carbon atoms, and $R_5$ represents hydrogen or methyl, $R_2$ represents, if X is oxygen, hydrogen or a hydroxybenzyl group of formula (II); if, however, X is —NH—, only hydrogen.

In the case where Y denotes an alkyl group, it can be a primary alkyl group, such as, e.g. a methyl, ethyl, n-propyl, n-butyl, n-hexyl, n-octyl, n-decyl or n-dodecyl group.

The symbols $R_3$ and $R_4$ can have the same meaning as R, but in addition represent a secondary or tertiary alkyl group, such as, e.g. a isopropyl, sec.butyl, 2-ethylhexyl, tert.butyl or tert.octyl group.

Where Y represents an alkenyl group, it can be, for example, an allyl or methallyl group. As an acyl group, $R_7$ can be an aliphatic acyl group, for example, an acetyl, propionyl, hexanoyl, acryl, methacryl, 2-ethyl-hexanoyl, dodecanoyl or octadecanoyl group, and also an aromatic acyl group, especially a benzoyl group.

These compounds impart to synthetic polymers excellent protection both against thermal-oxidative ageing and against light-induced ageing. As is known, organic polymers are slowly decomposed both by light and by oxygen, a factor which leads to a gradual falling off of the performance properties. This ageing is further accelerated by heat; on the other hand, it can be greatly retarded by the addition of stabilisers. It is known that hydroxybenzylmalonic acid derivatives can be used as anti-oxidative stabilisers for polymers; however, such compounds are completely lacking with regard to protective action against the effects of light rays. In this respect, however, it is also known that derivatives of 2,2,6,6-tetramethylpiperidine do act as light stabilisers, but on their own exhibit no perceptible antioxidative action. The said new compounds of formula I constitute a molecular combination of these two structures. Compared with a mixture of an anti-oxidant of the hydroxybenzylmalonic acid series and a light stabiliser of the tetramethylpiperidine series, the new compounds have the advantage of a more simple incorporation and of an overall uniformly constant ratio of anti-oxidant to light stabiliser. Surprisingly, however, there has been found yet another advantage; these new compounds have a greater stabilising action than that of the same amount of a mixture of a hydroxybenzylmalonic acid derivative and a tetramethylpiperidine derivative. This means in practice that the same effect can be obtained with a smaller amount of stabiliser.

Two classes are preferred among the compounds of formula (I): the one class is formed by the parahydroxybenzyl compounds such as those corresponding to formula (I) where $R_1$ represents a group of formula (IIa)

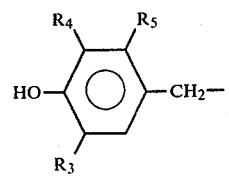

wherein $R_3$ denotes an isopropyl, tert.butyl or tert.amyl group, and $R_4$ denotes a methyl, ethyl, isopropyl, tert.butyl, tert.amyl or tert.octyl group, and where Y in formula (I) represents hydrogen, the radical —O. or a methyl, allyl or benzyl group.

Particularly preferred compounds among these are those in which $R_3$ represents a tertiary butyl group, $R_4$ represents a methyl or tert.butyl group, $R_5$ represents hydrogen, and Y hydrogen, the radical —O. or a methyl group.

The other class of preferred substances is the meta-hydroxybenzyl compounds. These correspond to formula (I) where $R_1$ represents a group of formula (IIb)

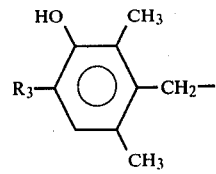

wherein $R_3$ denotes a tert.butyl, tert.amyl or tert.octyl group, and Y represents hydrogen, the radical —O. or a methyl group.

Examples of compounds of the first mentioned class are:
bis(3,5-di-tert.butyl-4-hydroxybenzyl)malonic acid-bis(2,2,6,6-tetramethyl-4-piperidinyl)ester,
bis(3,5-di-isopropyl-4-hydroxybenzyl)malonic acid-bis(2,2,6,6-tetramethyl-4-piperidinyl)ester,
bis(3-tert.butyl-4-hydroxy-5-methylbenzyl)malonic acid-bis(2,2,6,6-tetramethyl-4-piperidinyl-1-oxyl)ester,
3,5-di-tert.butyl-4-hydroxybenzylmalonic acid-bis(2,2,6,6-tetramethyl-4-piperidinyl-1-oxyl)ester,
3-tert.butyl-4-hydroxy-5,6-dimethylbenzylmalonic acid-bis(2,2,6,6-tetramethyl-4-piperidinyl)ester
3-tert.butyl-4-hydroxy-5,6-dimethylbenzylmalonic acid-bis(1,2,2,6,6-pentamethyl-4-piperidinyl)ester,
bis(3-tert.butyl-4-hydroxy-5,6-dimethylbenzyl)malonic acid-bis(2,2,6,6-tetramethyl-4-piperidinyl)ester,
bis(3-tert.butyl-4-hydroxy-5,6-dimethylbenzyl)malonic acid-bis(1,2,2,6,6-pentamethyl-4-piperidinyl)ester,
3-tert.butyl-4-hydroxy-5,6-dimethylbenzylmalonic acid-bis(2,2,6,6-tetramethyl-4-piperidinyl-1-oxyl)ester,
3-tert.butyl-4-hydroxy-5,6-dimethylbenzylmalonic acid-N,N'-bis-(2,2,6,6-tetramethyl-4-piperidinyl)amide,
bis-(3,5-di-tert.butyl-4-hydroxybenzyl)malonic acid-bis(1-octyl-2,2,6,6-tetramethyl-4-piperidinyl)ester,
3-tert.butyl-4-hydroxy-5,6-dimethylbenzylmalonic acid-bis(1-allyl-2,2,6,6-tetramethyl-4-piperidinyl)ester,
3,5-di-tert.butyl-4-hydroxybenzylmalonic acid-N,N'-bis-(2,2,6,6-tetramethyl-4-piperidinyl)-N,N'-dimethylamide,
3,5-di-tert.butyl-4-hydroxybenzylmalonic acid-bis-[1(2'-hydroxyethyl)2,2,6,6-tetramethyl-4-piperidinyl]ester.

Examples of compounds of the second-mentioned class are:
4-tert.butyl-3-hydroxy-2,6-dimethylbenzylmalonic acid-bis-(2,2,6,6-tetramethyl-4-piperidinyl)ester,
bis(4-tert.butyl-3-hydroxy-2,6-dimethylbenzyl)malonic acid-bis(2,2,6,6-tetramethyl-4-piperidinyl)ester,
4-tert.butyl-3-hydroxy-2,6-dimethylbenzylmalonic acid-bis-(2,2,6,6-pentamethyl-4-piperidinyl)ester,
bis(4-tert.butyl-3-hydroxy-2,6-dimethylbenzyl)malonic acid-bis(1,2,2,6,6-pentamethyl-4-piperidinyl)ester,
4-tert.butyl-3-hydroxy-2,6-dimethylbenzylmalonic acid-bis-(2,2,6,6-tetramethyl-4-piperidinyl)ester,
4-tert.butyl-3-hydroxy-2,6-dimethylbenzylmalonic acid-N-(1,2,2,6,6-pentamethyl-4-piperidinyl)amide,
bis(4-tert.butyl-3-hydroxy-2,6-dimethylbenzyl)malonic acid-bis(1-allyl-2,2,6,6-tetramethyl-4-piperidinyl)ester,
4-tert.butyl-3-hydroxy-2,6-dimethylbenzylmalonic acid-bis-(1-propargyl-2,2,6,6-tetramethyl-4-piperidinyl)ester,
4-tert.butyl-3-hydroxy-2,6-dimethylbenzylmalonic acid-bis[1(2'-acetoxyethyl)2,2,6,6-tetramethyl-4-piperidinyl]ester.

The compounds of formula (I) can be prepared by various processes. The most important process comprises the reaction of a malonic acid derivative of formula (III)

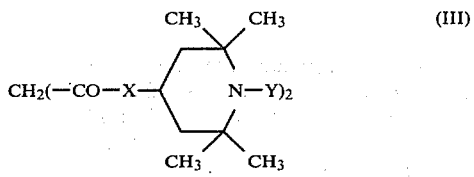

with, if X is oxygen, one mole or two moles, and, if X is —NH—, with one mole, of an N-dialkyldithiocarbaminate of formula (IV)

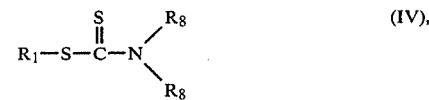

or of a hydroxybenzylamine of formula (V)

in the presence of a basic catalyst, whereby in the above formulae

X can be oxygen or —NH—,

Y represents hydrogen, the radical —O·, an alkyl group having 1 to 12 carbon atoms, an alkenyl group having 3 or 4 carbon atoms, a propargyl group, a benzyl group, or a group of the formula

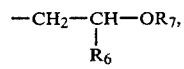

wherein $R_6$ represents hydrogen, methyl or phenyl, and $R_7$ represents hydrogen, or an acyl group having up to 18 carbon atoms, $R_1$ represents a hydroxybenzyl group of formula (II)

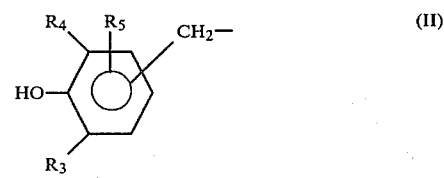

wherein $R_3$ and $R_4$ each independently represent an alkyl group having 1 to 8 carbon atoms, and $R_5$ represents hydrogen or methyl, and $R_8$ represents an alkyl group having 1 to 5 carbon atoms, or the two radicals $R_8$ together with the N-atom represent a morpholine, piperidine or pyrrolidine ring.

The starting substances of formula (III) are malonic acid esters and malonic acid amides of 4-hydroxy- and 4-aminotetramethylpiperidines, respectively. They are obtainable by standard processes; for example, by base-catalysed transesterification of diethylmalonate with 2 moles of a 4-hydroxy- or 4-aminotetramethylpiperidine. The compounds of formula (IV) are obtainable by reaction of a phenol of the formula R₁—H with formaldehyde, carbon disulphide and a secondary amine (R₈)₂NH.

The reaction of the components (III) and (IV) in the case of the esters (X=O) can be performed in the molar ratio of 1:1 or 1:2. In the first case are obtained the monohydroxybenzyl compounds of formula (I) wherein R₂=H, and in the second case the di-hydroxybenzyl compounds of formula (I) wherein R₂=R₁. With regard to the amides (X=—NH—), the reaction ceases, even with use of more than 1 mole (IV), at the first stage, so that here there are obtained only the final products wherein R₂=H. Suitable basic catalysts are, for example, alkali hydroxides such as NaOH or KOH, alkali or alkaline-earth alcoholates such as CH₃ONa, C₂H₅ONa, (CH₃)₃COK, (C₂H₅O)₂Mg or (CH₃)₂CHOLi, alkali hydrides or alkaline-earth hydrides such as LiH, NaH or CaH₂, and alkali amides such as NaNH₂, LiNH₂ or KNH₂. Those preferably used are alkali hydroxides. These bases are preferably employed in equimolar amounts, i.e. per mole of dithiocarbaminate is used one mole-equivalent of the base. The reaction can be performed in solution; this method ensures better temperature control, and is to be particularly recommended with high-melting starting components. Suitable solvents are, for example, alcohols, such as methanol, ethanol, isopropanol or tert.butanol; also suitable are aliphatic ethers or cyclic ethers, such as diethyl ether, tetrahydrofuran or dioxane; also hydrocarbons such as hexane, heptane, ligroin, decalin, cyclohexane, benzene, toluene or xylene, as well as polar aprotic solvents, such as dimethylformamide, dimethylacetamide or dimethylsulphoxide. The last-mentioned group of solvents is to recommended, in particular, with use of the malonamide of formula (II), X=NH.

Instead of using dithiocarbaminates, it is possible to use the corresponding hydroxybenzylamines of formula (V). In this case too, the reaction can be performed with or without solvents, whereby likewise the above-mentioned solvents are suitable. And also with respect to catalysts, the same basic substances as described above are applicable. It is preferable to use alkali amides and alkali alcoholates. They are applied in catalytic amounts, i.e. approximately in amounts of 0.1 to 5 Mol-%. Use of larger amounts of the base is of no advantage.

A further process for the preparation of compounds of formula (I) consists in the reaction of a malonic acid dialkyl ester of formula (VI) with two moles of a tetramethylpiperidine derivative of formula (VII):

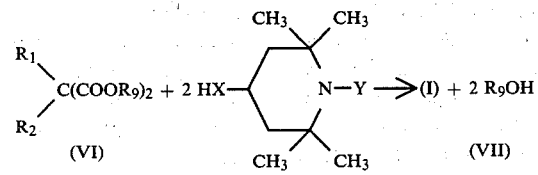

The symbol R₉ in the formula represents an alkyl radical having 1 to 4 carbon atoms. Suitable bases as catalysts are the same as those described previously. In this process too, the reaction can be performed in a solvent, whereby, with the exception of the alcohols, all the previously mentioned groups of solvents are suitable.

In all the processes discussed here, the reaction is normally performed at elevated temperature, in order to ensure a rapid and complete course of reaction. Isolation of the products can be carried out by the usual methods, for example, by concentration through evaporation, and crystallisation of the residue. It is advantageous for the base to be neutralised before the solvent is distilled off.

According to the present invention, the compounds of formula (I) can be used as stabilisers for organic polymers. Such organic polymers are, for example:

1. Polymers which are derived from hydrocarbons with single or double unsaturation, e.g. polyolefins such as polyethylene, which can be optionally cross-linked, polypropylene, polybutene-1, polyisobutene, polymethylbutene-1, polymethylpentene-1, polyisoprene, polybutadiene, polystyrene, copolymers of the monomers on which the mentioned homopolymers are based, such as ethylenepropylene copolymers, propylene-butene-1 copolymers, propylene-isobutene copolymers, styrene-butadiene copolymers, as well as terpolymers of ethylene and propylene with a diene, such as, e.g. hexadiene, dicyclopentadiene or ethylidenenorbornene; mixtures of the above given homopolymers, such as, for example, mixtures of polypropylene and polyethylene, polypropylene and polybutene-1, polypropylene and polyisobutylene, or of butadiene-acrylonitrile copolymerisate with a styrene-butadiene copolymerisate.

2. Halogen-containing vinylpolymers, such as polyvinyl chloride, polyvinylidene chloride, polyvinylfluoride, polychloroprene and chlorinated rubbers.

3. Polymers derived from α,β-unsaturated acids and their derivatives, such as polyacrylates and polymethacrylates, polyacrylamides and polyacrylnitrile, as well as copolymers with other vinyl compounds, such as acrylonitrile/butadiene/styrene, acrylonitrile/styrene and acrylonitrile/styrene/acrylic ester copolymers.

4. Polymers derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.

5. Homopolymers and copolymers derived from epoxides, such as polyethylene oxide, or the polymerisates which are derived from bis-glycidyl ethers.

6. Polyacetals, such as polyoxymethylene and polyoxyethylene, as well as those polyoxymethylenes which contain ethylene oxide as the comonomer.

7. Polyphenylene oxides.

8. Polyurethanes and polyureas.

9. Polycarbonates.

10. Polysulphones.

11. Polyamides and copolyamides derived from diamines and dicarboxylic acids and/or from aminocarboxylic acids or the corresponding lactams, such as polyamide 6, polyamide 6/6, polyamide 6/10, polyamide 11 and polyamide 12.

12. Polyesters derived from dicarboxylic acids and dialcohols and/or from hydroxycarboxylic acids or the corresponding lactones, such as polyethylene glycol terephthalate, polybutylene terephthalate, poly-1,4-dimethylol-cyclohexane terephthalate, as well as their starting materials, such as lower terephthalic acid alkyl esters.

13. Cross-linked polymerisates which are derived from aldehydes on the one hand, and from phenols, ureas and melamines on the other, such as phenol-formaldehyde resins, urea-formaldehyde resins and melamine-formaldehyde resins.

14. Alkyd resins, such as glycerin-phthalic acid resins and mixtures thereof with melamine-formaldehyde resins.

15. Unsaturated polyester resins derived from co-polyesters of saturated and unsaturated dicarboxylic acids with polyvalent alcohols, as well as vinyl compounds as cross-linking agents, and also their halogen-containing, difficulty combustible modifications.

16. Natural polymers, such as cellulose, rubber and proteins, as well as their polymer-homologously chemically modified derivatives, such as cellulose acetates, cellulose propionates and cellulose butyrates, or cellulose ethers, such as methylcellulose.

Preferred polymers are polyethylene of high and low density, polypropylene, polybutadiene, polyurethanes, polystyrene and its copolymers, as well as mixtures thereof.

The new compounds are added to the substrates in a concentration of 0.01 to 5 percent by weight, calculated on the material to be stabilised. Preferably, 0.05 to 1.5, particularly preferably 0.1 to 0.8, percent by weight of the compounds, calculated on the material to be stabilised, is incorporated into the said material.

Incorporation can be effected after polymerisation; for example, by the mixing of the compounds and, optionally, further additives into the melt, by methods common in practice, before or during moulding (shaping); or by application of the dissolved or dispersed compounds to the polymers, optionally with subsequent removal of the solvent by evaporation.

The new compounds can also be added in the form of a master batch, containing these compounds in a concentration of, for example, 2.5 to 25 percent by weight, to the polymers to be stabilised.

In the case of cross-linked polyethylene, the compounds are added before cross-linking.

In addition to the compounds of formula (I), other known stabilisers may be added to the polymers, or other additives commonly used in plastics technology, such as, e.g. flame-retarding agents, antistatic agents, plasticisers, lubricants, expanding agents, pigments or fillers.

The preparation and use of the compounds according to the invention is further illustrated in the following examples. The term 'parts' denotes parts by weight and % percent by weight; temperatures are expressed in degrees Centigrade.

EXAMPLE 1

12.3 g (0.03 mole) of bis-(1,2,2,6,6-pentamethyl-4-piperidinyl)malonate and 19.5 g (0.06 mole) of N-diethyl-S-(3-methyl-5-tert.-butyl-4-hydroxybenzyl)dithiocarbaminate are dissolved in 100 ml of isopropanol. An addition is made dropwise at 60° in the course of 15 minutes, with stirring, of 2.4 g of NaOH (0.06 mole) in 12 ml of water. The whole is subsequently refluxed for 2 hours and then cooled to 50°; an amount of 72 ml of 1% acetic acid is added and the mixture cooled to 0°. The product thereupon crystallises out and is recrystallised from ligroin to thus obtain 18.7 g (85.7% of theory) of bis-(3-methyl-5-tert.butyl-4-hydroxybenzyl)malonic acid-bis-(1,2,2,6,6-pentamethyl-4-piperidinyl)ester, M.P. 150°.

EXAMPLES 2 to 5

As described in Example 1, 1 mole of a malonic acid ester of formula (IIIa) is in each case reacted with two moles of an N-diethyldithiocarbaminate of formula (IVa) and two moles of sodium hydroxide solution, with the products listed in the following Table 1 being obtained.

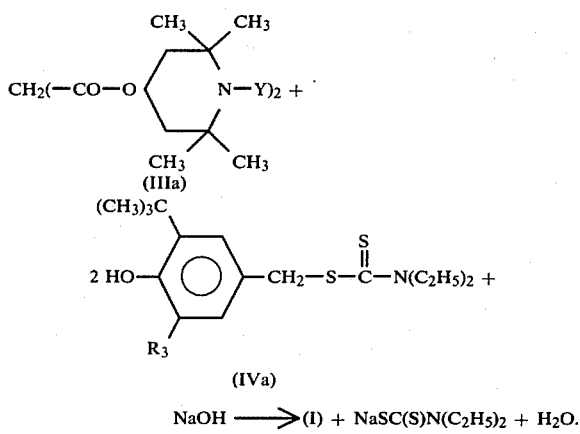

NaOH ⟶ (I) + NaSC(S)N(C$_2$H$_5$)$_2$ + H$_2$O.

TABLE I

| Test No. | Y | R$_3$ | Product | M.P. |
|---|---|---|---|---|
| 2 | CH$_3$ | t-C$_4$H$_9$ | bis(3,5-di-tert.butyl-4-hydroxybenzyl)malonic acid-bis(1,2,2,6,6-pentamethyl-4-piperidinyl)ester | 239° C. |
| 3 | H | CH$_3$ | bis(3-methyl-5-tert.butyl-4-hydroxybenzyl)malonic acid-bis(2,2,6,6-tetramethyl-4-piperidinyl)ester | 171° C. |
| 4 | O | t-C$_4$H$_9$ | bis(3,5-di-tert.butyl-4-hydroxybenzyl)malonic acid-bis(2,2,6,6-tetramethyl-4-piperidinyl-1-oxyl)ester | 225° C. |
| 5 | H | t-C$_4$H$_9$ | bis(3,5-di-tert.butyl-4-hydroxybenzyl)malonic acid-bis(2,2,6,6-tetramethyl-4-piperidinyl)ester | 205° C. |

EXAMPLE 6

26 g (0.068 mole) of bis-(2,2,6,6-tetramethyl-4-piperidinyl) malonate and 17.8 g (0.068 mole) of N-(3,5-di-tert.butyl-4-hydroxybenzyl)dimethylamine are dissolved in 200 ml of toluene. After the addition of 0.5 g of lithium amide, the mixture is refluxed for 3 hours. After cooling, the mixture is neutralised with 1.5 ml of 1% acetic acid, and the organic phase repeatedly washed with water. After drying over Na$_2$SO$_4$, the solution is concentrated in vacuo to obtain, as oily residue, 3,5-di-tert.butyl-4-hydroxybenzyl-malonic acid-bis(2,2,6,6-tetramethyl-4-piperidinyl)ester.

EXAMPLES 7 to 11

The products described in Table 2 are obtained analogously to Example 5, the procedure in this case being that in each test a malonic acid derivative of formula (III) is reacted with one mole of a hydroxybenzylamine of formula Va.

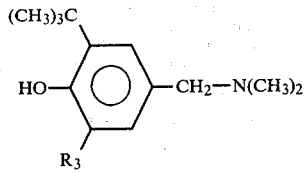

(Va)

TABLE 2

| Test No. | X | Y | R₃ | Product | M.P. |
|---|---|---|---|---|---|
| 7 | O | H | CH₃ | 3-methyl-5-tert. butyl-4-hydroxy-benzylmalonic acid-bis(2,2,6,6-tetramethyl-4-piperidinyl)ester | oily residue |
| 8 | O | CH₃ | CH₃ | 3-methyl-5-tert. butyl-4-hydroxy-benzylmalonic acid-bis(1,2,2,6,6-pentamethyl-4-piperidinyl)ester. | 105° |
| 9 | O | CH₃ | t-C₄H₉ | 3,5-di-tert.butyl-hydroxybenzylmalonic acid-bis(1,2,2,6,6-pentamethyl-4-piperidinyl)ester | oily residue |
| 10 | NH | H | t-C₄H₉ | 3,5-di-tert.butyl-4-hydroxybenzylmalonic acid-bis(2,2,6,6-tetramethyl-4-piperidinyl)amide | 253° |
| 11 | NH | H | CH₃ | 3-methyl-5-tert. butyl-4-hydroxybenzylmalonic acid-bis(2,2,6,6-tertamethyl-4-piperidinyl)amide | 200° |

EXAMPLE 12

24.5 g (0.076 mole) of 3,5-di-isopropyl-4-hydroxybenzylmalonic acid dimethyl ester and 23.8 g (0.15 mole) of 4-hydroxy-2,2,6,6-tetramethylpiperidine are dissolved in 40 ml of xylene. An addition is made to the solution, heated to 125°–130°, of 0.2 g of lithium amide, with stirring; the solution is subsequently refluxed for 2 hours; it is then cooled to about 50°, and neutralised with 0.8 ml of 1% acetic acid; the organic phase is washed with water and dried over Na₂SO₄. After concentration in vacuo, there is obtained, as residue, 3,5-di-isopropyl-4-hydroxybenzylmalonic acid-bis(2,2,6,6-tetramethyl-4-piperidinyl)ester, M.P. 123°.

EXAMPLE 13

100 Parts of polypropylene (melting index 3.2 g/10 min., 230°/2160 g) are intensively mixed, in a shaking apparatus, with 0.2 parts of one of the additives listed in the following Table 3 for 10 minutes. The resulting mixture is kneaded in a Brabender plastograph at 200° for 10 minutes; the mixture thus obtained is subsequently pressed out in a platen press, with 260° platen temperature, to obtain 1 mm thick sheets, from which are stamped strips 1 cm in width and 17 cm in length.

The testing of the effectiveness of the additives incorporated in the test strips is performed by heat ageing in an air-circulation furnace at 135° and 149°, with an additive-free test strip serving as a comparison. Three test strips are used from each formulation. The final point is defined as being that at which there commences an easily visible crumbling of the test strip.

TABLE 3

| Stabiliser Ex. No. | Days to commencement of decomposition | |
|---|---|---|
| | 149° | 135° |
| none | 1 | 3 |
| 1 | 34 | 140 |
| 2 | 24 | 37 |
| 3 | 21 | 86 |
| 5 | 20 | 68 |
| 8 | 17 | 48 |

EXAMPLE 14

100 Parts of polypropylene (melting index 3.2 g/10 min., 230°/2160 g) are intensively mixed, in a shaking apparatus, with 0.1 part of one of the additives listed in the following Table 4 and 0.3 part of dilaurylthiopropionate for 10 minutes. The resulting mixture is kneaded in a Brabender plastograph at 200° for 10 minutes: the mixture thus obtained is subsequently pressed out in a platen press, with 260° platen temperature, to produce 1 mm thick sheets, from which are stamped strips 1 cm in width and 17 cm in length.

The testing of the effectiveness of the additives incorporated in the test strips is performed by heat ageing in an air-circulation furnace at 135° and 149°, whereby a test strip containing just the 0.3 part of dilaurylthiodipropionate is taken as a comparison. Three test strips are used from each formulation. The final point is defined as being that at which there commences an easily visible decomposition of the test strip.

Table 4

| Stabiliser Example No. | Days to commencement of decomposition | |
|---|---|---|
| | 149° | 135° |
| Comparison | 5 | 11 |
| 1 | 56 | 130 |
| 2 | 48 | 110 |
| 3 | 37 | 86 |

EXAMPLE 15

The specimens described in Example 13 were tested also with respect to their colour stability as follows:

(a) after incorporation (Table 5, col. 2), (b) after 500 hours exposure in a Xenotest apparatus of the film Hanau (Table 5, col. 3), and (c) after 1-week's treatment with boiling water (Table 5, col. 4).

There was used for Table 5 an empirical colour scale in which 5 denotes colourlessness, 4 a barely perceptible slight discolouration, and 3, 2 and 1 denote a successively greater discolouration.

Table 5

| Stabiliser Example No. | Colour assessment according to the Scale 1-5 | | |
|---|---|---|---|
| | after incorporation | after exposure | boiling water 1 week |
| 1 | 5 | 5 | 4–5 |
| 2 | 5 | 5 | 5 |
| 3 | 5 | 5 | 4–5 |

EXAMPLE 16

100 Parts of polypropylene (melting index 19 g/10 min., 230°/2160 g) are intensively mixed for 10 minutes, in a shaking apparatus, with 0.1 part of one of the stabilisers obtained according to Example 4 or Example 6.

The resulting mixture is extruded in a laboratory single screw extruder ("Plamvo") at 260° nozzle temperature, 100 r.p.m. and a throughput of 50 g/min, and subsequently granulated. The resulting granulate is spun in a spinning apparatus, with a nozzle temperature of 280°, into polyfilaments, which are then stretched in the ratio of 1:5.5. These filaments are subjected to a gas-fading test analogously to the AATCC Standard 23-1957, the test consisting in the exposure of the specimens to the exhaust gases of a butane-gas burner at 60° for 24 hours.

A visual assessment of colouration shows in both cases that the specimens have remained colourless.

EXAMPLE 17

From the 1 mm thick test sheets described in Example 13 are cut, with the aid of a Mikrotom, chips (clippings) having a thickness of $25\mu$. These clippings are clamped between pieces of stainless-steel mesh, and the thus formed carriers then suspended in an air-circulation furnace and aged at 135° and 147°, respectively. The end point is defined as being the time after which, with slight tapping of the mesh containers, decomposed polypropylene falls out in powder form (control 1—2× daily). The results are given in hours (Table 6).

TABLE 6

| Stabiliser Example No. | Hours to commencement of decomposition | |
|---|---|---|
| | at 147° | at 135° |
| without additive | 10 | 20 |
| 1 | 120 | 280 |
| 2 | 70 | 210 |
| 3 | 45 | 140 |

EXAMPLE 18

Chips (clippings) $25\mu$ thick are cut, with the aid of a Mikrotom, from the 1 mm thick test sheets described in Example 14. These clippings are clamped between pieces of stainless-steel mesh, and the thus formed carriers then suspended in an air-circulation furnace and aged at 135° and 147°, respectively. The end point is defined as being the time at which, on slight tapping of the mesh containers, decomposed polypropylene falls out in powder form (control 1—2× daily). The results are given in hours (Table 7).

TABLE 7

| Stabiliser Example No. | Hours to commencement of decomposition | |
|---|---|---|
| | at 147° | at 135° |
| Comparison | 10 | 20 |
| 1 | 120 | 280 |
| 2 | 140 | 285 |
| 3 | 120 | 280 |

EXAMPLE 19

100 Parts of polypropylene powder (Moplen Fibre grade, of the firm Montedison) with 0.2 parts of β-(3,5-ditert. butyl-4-hydroxyphenyl)propionic acid octadecyl ester and 0.25 part of a stabiliser from the following Table 8 are homogenised in a Brabender plastograph at 200° C. for 10 minutes. The resulting mixture is removed as quickly as possible from the kneader, and moulded in a toggle press into the form of 2–3 mm thick sheet. A portion of the moulded sheet thus obtained is cut out and then pressed out between two high-gloss hard aluminum sheets under a hand-hydraulic laboratory press for 6 minutes at 260° with a pressure of 12 tons to give a sheet 0.5 mm in thickness, which is immediately quenched in cold water. From this 0.5 mm sheet is then prepared, under exactly the same conditions, the 0.1 mm thick test sheet material. Specimens each 60×44 mm in size are stamped out from this material and irradiated in the Xenotest 150. These specimens are removed at regular intervals of time from the exposure apparatus and their carbonyl content measured in an IR-spectrophotometer. The increase of the carbonyl extinction on exposure to light is a measure for the photooxidative decomposition of the polymer [cp. L. Balaban et al., J Polymer Sci. Part C, 22, 1059–1071 (1969); J. F. Heacock, J. Polymer Sci. Part A-1, 22, 2921–34 (1969); D. J. Carlsson and D. M. Wiles, Macromolecules 2, 587–606 (1969)] and, as known from experience, is associated with a decline of the mechanical properties of the polymer. Thus, for example, the comparison sheet (stabilised only with antioxidant) is completely brittle on attainment of a carbonyl extinction of ca. 0.300.

The protective action of the stabilisers according to the invention is clearly shown by the following Table 8.

Table 8

| Stabiliser Example No. | Exposure time in hours | CO-Extinction (5.85 $\mu$) |
|---|---|---|
| Comparison | 800 | 0.30 |
| 1 | >6000 | 0.010 |
| 2 | >6000 | 0.010 |
| 7 | >5000 | 0.010 |
| 10 | >5000 | 0.010 |

EXAMPLE 20

100 Parts of polystyrene granules are mixed dry with 0.25 parts of a stabiliser from the following Table 9; the mixture is then re-granulated in an extruder, and subsequently processed, in an injection-moulding machine, into the form of sheets 2 mm in thickness. The sheets thus obtained are afterwards irradiated for 2000 hours in a Xenotest apparatus 150, and their yellowing values determined by means of the yellowing factor in the following manner:

$$\text{yellowing factor } (Y.F.) = \frac{\Delta T(420) - \Delta T(680)}{T(560)} \times 100,$$

whereby $\Delta T$ denotes the transmission loss with the wave lengths 420 and 680 nm during exposure of the specimens, and T (560) is the transmission value as a percentage of the value in the case of the unexposed speciment at 560 nm.

Table 9

| Stabiliser Example No. | Y.F. |
|---|---|
| No stabiliser | 20.0 |
| 1 | 4.5 |
| 6 | 5.5 |

We claim:
1. A composition of matter comprising an organic polymer normally subject to degradation by oxidation, light or heat, and as a stabilizer from 0.01 to 5% of at least one compound of the formula

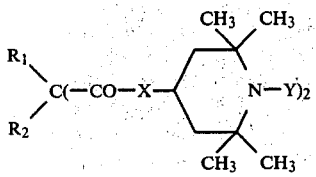

(I)

wherein
X can be oxygen or —NH—,
Y represents hydrogen, the radical —O., an alkyl group having 1 to 12 carbon atoms, an alkenyl group having 3 or 4 carbon atoms, a propargyl group, a benzyl group, or a group of the formula

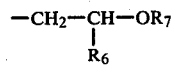

wherein $R_6$ represents hydrogen, methyl or phenyl, and $R_7$ represents hydrogen, or an acyl group selected from the group consisting of acetyl, propionyl, hexanoyl, acryl, methacryl, 2-ethylhexanoyl, dodecanoyl, octadecanoyl and benzoyl,
$R_1$ represents a hydroxybenzyl group of formula (II)

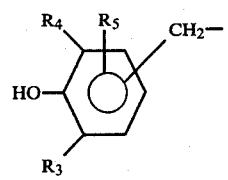

(II)

wherein
$R_3$ and $R_4$ each independently represent an alkyl group having 1 to 8 carbon atoms, and
$R_5$ represents hydrogen or methyl, and
$R_2$ represents, if X is oxygen, hydrogen, or a hydroxybenzyl group of formula (II); if however, X is —NH—, only hydrogen.

2. A composition of claim 1 wherein
Y represents hydrogen, the radical —O., methyl, allyl or benzyl group, and
$R_1$ represents a hydroxybenzyl group of the formula

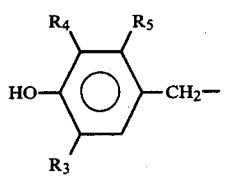

wherein
$R_3$ represents isopropyl, tert.butyl or tert.amyl group,
$R_4$ represents methyl, ethyl, isopropyl, tert.butyl, tert.amyl or tert.octyl group, and
$R_5$ represents hydrogen or methyl.

3. A composition of claim 1 wherein
Y represents hydrogen, the radical —O. or methyl group,
$R_3$ represents tert.butyl group,
$R_4$ represents methyl or tert.butyl group, and
$R_5$ represents hydrogen.

4. A composition of matter according to claim 1, where the polymer is a polyolefin.

5. A composition of claim 1 wherein
Y represents hydrogen, the radical —O. or methyl group, and
$R_1$ represents a hydroxybenzyl group of formula (IIb)

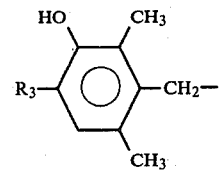

(IIb)

wherein $R_3$ represents tert.butyl, tert.amyl or tert.octyl group.

6. A composition of claim 4 stabilized with bis(2,2,6,6-tetramethyl-4-piperidinyl) ester of bis(3,5-di-tert.butyl-4-hydroxybenzyl)malonic acid.

7. A composition of claim 4 stabilized with bis(1,2,2,6,6-pentamethyl-4-piperidinyl) ester of bis(3-methyl-5-tert.butyl-4-hydroxybenzyl)malonic acid.

8. A composition of claim 4 stabilized with bis(1,2,2,6,6-pentamethyl-4-piperidinyl) ester of bis(3,5-di-tert.butyl-4-hydroxybenzyl)malonic acid.

9. A composition of claim 4 stabilized with bis(2,2,6,6-tetramethyl-4-piperidinyl) ester of 3-methyl-5-tert.butyl-4-hydroxybenzylmalonic acid.

10. Method for stabilizing organic polymers against thermal oxidative and light-induced ageing by adding to the polymer 0.01 to 5 percent by weight of at least one compound of formula (I)

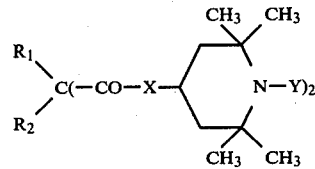

(I)

wherein
X can be oxygen or —NH—,
Y represents hydrogen, the radical —O., an alkyl group having 1 to 12 carbon atoms, an alkenyl group having 3 or 4 carbon atoms, a propargyl group, a benzyl group, or a group of the formula

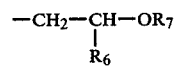

wherein $R_6$ represents hydrogen, methyl or phenyl, and $R_7$ represents hydrogen, or an acyl group selected from the group consisting of acetyl, propionyl, hexanoyl, acryl, methacryl, 2-ethyl-hexanoyl, dodecanoyl, octadecanoyl and benzoyl,
$R_1$ represents a hydroxybenzyl group of formula (II)

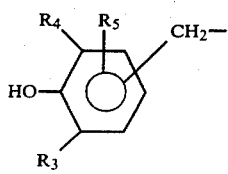 (II)
wherein
R$_3$ and R$_4$ each independently represent an alkyl group having 1 to 8 carbon atoms, and
R$_5$ represents hydrogen or methyl, and
R$_2$ represents, if X is oxygen, hydrogen, or a hydroxybenzyl group of formula (II); if, however, X is —NH—, only hydrogen.
11. Method according to claim 10, wherein the polymer is a polyolefin.
* * * * *